United States Patent
Pillow

(10) Patent No.: US 9,293,709 B2
(45) Date of Patent: Mar. 22, 2016

(54) POLYMER

(75) Inventor: Jonathan Pillow, Stotfold (GB)

(73) Assignees: Cambridge Display Technology, Ltd., Godmanchester (DE); Sumitomo Chemical Company Limited, Tokyo (JP)

(*) Notice: Subject to any disclaimer, the term of this patent is extended or adjusted under 35 U.S.C. 154(b) by 0 days.

(21) Appl. No.: 13/982,728

(22) PCT Filed: Jan. 26, 2012

(86) PCT No.: PCT/GB2012/000080
§ 371 (c)(1),
(2), (4) Date: Oct. 21, 2013

(87) PCT Pub. No.: WO2012/104579
PCT Pub. Date: Aug. 9, 2012

(65) Prior Publication Data
US 2014/0039148 A1   Feb. 6, 2014

(30) Foreign Application Priority Data

Jan. 31, 2011 (GB) .................................. 1101641.7

(51) Int. Cl.
*H01L 51/00* (2006.01)
*C08G 61/02* (2006.01)
(Continued)

(52) U.S. Cl.
CPC ............ *H01L 51/0043* (2013.01); *C07C 25/22* (2013.01); *C07C 35/52* (2013.01);
(Continued)

(58) Field of Classification Search
CPC ............... C08G 2261/3142; C01L 51/0043
USPC ............... 528/8, 394, 395, 396, 397; 568/3
See application file for complete search history.

(56) References Cited

U.S. PATENT DOCUMENTS 5,150,006 A   9/1992   Van Slyke et al.
5,432,014 A   7/1995   Sano et al.
(Continued)

FOREIGN PATENT DOCUMENTS

DE   19846767 A1   4/2000
EP   0880303 A1   11/1998
(Continued)

OTHER PUBLICATIONS

Setayesh, S., et al., "Polyfluorenes with polyphenylene dendron side chains: toward non-aggregating, light-emitting polymers," J. Am. Chem. Soc., 2001, 123, 946-953.*
(Continued)

*Primary Examiner* — Nicholas Hill
(74) *Attorney, Agent, or Firm* — Wolf, Greenfield & Sacks, P.C.

(57) ABSTRACT

A polymer, for use in an organic light emitting device, comprises asymmetrically substituted repeat units of formula (I (a)): wherein R7 represents a substituent bound to the 9-carbon atom of the fluorene ring through a non-aromatic carbon atom, $R^8$, $R^9$ and $R^{11}$ independently in each occurrence represent H or a substituent with the proviso that at least one $R^8$ is not H; $R^{10}$ independently in each occurrence is a substituent; and t in each occurrence is independently 0, 1, 2 or 3. $R^7$ is preferably a linear alkyl substituted with one or more groups —$(Ar^6)w$, wherein each $Ar^6$ independently represents an optionally substituted aryl or heteroaryl group, and w is at least 1, for example 1, 2 or 3.

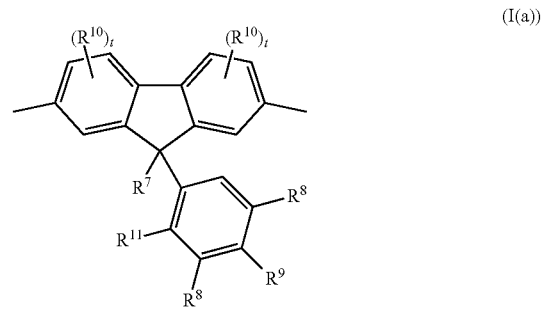

(I(a))

19 Claims, 2 Drawing Sheets

(51) Int. Cl.
*C08G 61/12* (2006.01)
*C07C 35/52* (2006.01)
*C07C 25/22* (2006.01)
*C09K 11/06* (2006.01)
*H05B 33/14* (2006.01)

(52) U.S. Cl.
CPC .............. *C08G 61/02* (2013.01); *C08G 61/12* (2013.01); *C09K 11/06* (2013.01); *H01L 51/0039* (2013.01); *H05B 33/14* (2013.01); *C07C 2103/18* (2013.01); *C08G 2261/3142* (2013.01); *C08G 2261/3162* (2013.01); *C08G 2261/5222* (2013.01); *C09K 2211/1416* (2013.01)

(56) References Cited

U.S. PATENT DOCUMENTS

| | | | |
|---|---|---|---|
| 5,723,873 | A | 3/1998 | Yang |
| 5,798,170 | A | 8/1998 | Zhang et al. |
| 6,083,634 | A | 7/2000 | Shi |
| 6,268,695 | B1 | 7/2001 | Affinito |
| 6,353,083 | B1 | 3/2002 | Inbasekaran et al. |
| 6,653,438 | B1 * | 11/2003 | Spreitzer et al. ............ 528/394 |
| 2002/0117662 | A1 | 8/2002 | Nii |
| 2002/0182441 | A1 | 12/2002 | Lamansky et al. |
| 2004/0054152 | A1 * | 3/2004 | Meerholz et al. ............ 534/15 |
| 2011/0127517 | A1 * | 6/2011 | Nakatani .................... 257/40 |

FOREIGN PATENT DOCUMENTS

| | | |
|---|---|---|
| EP | 0901176 A2 | 3/1999 |
| EP | 0947123 A1 | 10/1999 |
| EP | 0949850 A1 | 10/1999 |
| EP | 1245659 A1 | 10/2002 |
| GB | 2348316 A | 9/2000 |
| JP | 2002-324679 A | 11/2002 |
| WO | WO 98/10621 A1 | 3/1998 |
| WO | WO 98/57381 A1 | 12/1998 |
| WO | WO 99/54385 A1 | 10/1999 |
| WO | WO 00/48258 A1 | 8/2000 |
| WO | WO 00/53656 A1 | 9/2000 |
| WO | WO 00/55927 A1 | 9/2000 |
| WO | WO 01/19142 A1 | 3/2001 |
| WO | WO 01/81649 A1 | 11/2001 |
| WO | WO 02/31896 A2 | 4/2002 |
| WO | WO 02/44189 A1 | 6/2002 |
| WO | WO 02/45466 A1 | 6/2002 |
| WO | WO 02/066552 A1 | 8/2002 |
| WO | WO 02/068435 A1 | 9/2002 |
| WO | WO 02/081448 A1 | 10/2002 |
| WO | WO 02/084759 A1 | 10/2002 |
| WO | WO 02/092723 A1 | 11/2002 |
| WO | WO 03/018653 A1 | 3/2003 |
| WO | WO 03/022908 A1 | 3/2003 |
| WO | WO 2004039912 A1 * | 5/2004 |
| WO | WO 2009/066061 A1 | 5/2009 |
| WO | WO 2010/001982 A1 | 1/2010 |
| WO | WO 2010013724 A1 * | 2/2010 |
| WO | WO 2011/161417 A1 | 12/2011 |
| WO | WO 2011/161425 A1 | 12/2011 |

OTHER PUBLICATIONS

Grimsdale, A. C., et al., "Correlation between molecular structure, microscopic morphology, and optical properties of poly(tetraalkylindnofluorene)s," Adv. Funct. Mater., 2002, 12, 729-733.*

International Search Report and Written Opinion for PCT/GB2012/000080 mailed May 23, 2012.

International Preliminary Report on Patentability for PCT/GB2012/000080 mailed Aug. 15, 2013.

Chen et al., Recent developments in molecular organic electroluminescent materials. Macromol Symp. 1997;125:1-48.

Michaelson, The work function of the elements and its periodicity. J. Appl. Phys. 1977;48(11):4729-4733.

Niu et al., Thermal annealing below the glass transition temperature: A general way to increase performance of light-emitting diodes based on copolyfluorenes. Appl. Phys. Lett. 2002;81(4):634-636.

Tokito et al., Metal oxides as a hole-injecting layer for an organic electroluminescent device. Journal of Physics D: Applied Physics. 1996;29(11):2750-2753.

Yamamoto, Electrically Conducting and Thermally Stable π—Conjugated Poly(arylene)s Prepared by Organometallic Processes. Progress in Polymer Science. 1993;17:1153-1205.

Yang et al., Efficient polymer light emitting diodes with metal fluoride/Al cathodes. Appl Phys Lett. Jul. 30, 2001;79(5):563-5.

* cited by examiner

POLYMER

RELATED APPLICATIONS

The present application is a national stage filing under 35 U.S.C. §371 of international PCT application, PCT/GB2012/000080, filed Jan. 26, 2012, which claims priority to United Kingdom patent application, GB 1101641.7, filed Jan. 31, 2011, which is incorporated herein by reference.

FIELD OF THE INVENTION

The present invention relates to polymers for use in organic light emitting devices, comprising asymmetrically substituted repeat units, methods of making said polymers and devices comprising said polymers.

BACKGROUND

Electronic devices comprising active organic materials are attracting increasing attention for use in devices such as organic light emitting diodes (OLEDs), organic photoresponsive devices (in particular organic photovoltaic devices and organic photosensors), organic transistors and memory array devices. Devices comprising organic materials offer benefits such as low weight, low power consumption and flexibility. Moreover, use of soluble organic materials allows use of solution processing in device manufacture, for example inkjet printing or spin-coating.

With reference to FIG. 1, an OLED may comprise a substrate 1 carrying an anode 2, a cathode 4 and an organic light-emitting layer 3 between the anode and cathode.

Holes are injected into the device through the anode 2 and electrons are injected through the cathode 4 during operation of the device. Holes in the highest occupied molecular orbital (HOMO) and electrons in the lowest unoccupied molecular orbital (LUMO) of a light-emitting material in the light-emitting layer combine to form an exciton that releases its energy as light.

Suitable light-emitting materials include small molecule, polymeric and dendrimeric materials. Suitable light-emitting polymers for use in layer 3 include poly(arylene vinylenes) such as poly(p-phenylene vinylenes) and polyarylenes such as polyfluorenes.

Polymers comprising 9,9-dialkyl substituted fluorene repeat units are disclosed in, for example, WO 99/54385.

WO 02/092723 discloses polymers comprising 9,9-diaryl substituted fluorene repeat units, which are reported to have longer lifetime that analogous polymers comprising 9,9-dialkyl substituted fluorene repeat units. This increased lifetime is attributed to an increase in thermal stability of the polymer when 9,9-dialkyl substituents are replaced with 9,9-diaryl substituents, which is manifested in higher polymer glass transition temperatures ("lifetime" as used herein means the time taken for luminance of a polymer to fall by a specified percentage, for example 10% or 50%, at constant current).

DE 19846767 discloses a 9-alkyl-9-aryl fluorene monomer.

WO 2004/039912 discloses a method of forming fluorenes with different substituents in the 9-position, such as a 9-alkyl-9-phenyl fluorenes.

WO 2009/066061 discloses a hole transport layer comprising a polymer having a repeat unit comprising a 9,9 biphenyl fluorene repeat unit wherein the 9-phenyl rings are independently and optionally substituted.

SUMMARY OF THE INVENTION

In a first aspect the invention provides a polymer comprising a repeat unit of formula (Ia):

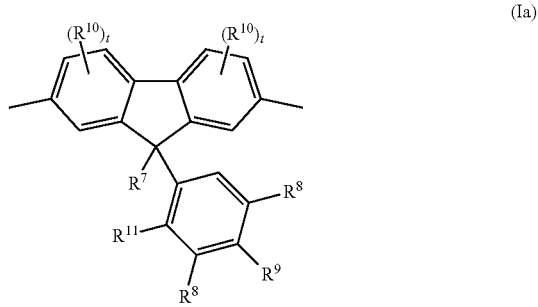

wherein $R^7$ represents a substituent bound to the 9-carbon atom of the fluorene ring through a non-aromatic carbon atom, $R^8$, $R^9$ and $R^{11}$ independently in each occurrence represent H or a substituent with the proviso that at least one $R^8$ is not H; $R^{10}$ independently in each occurrence is a substituent; and t in each occurrence is independently 0, 1, 2 or 3.

Optionally, $R^7$ is substituted or unsubstituted alkyl, optionally linear alkyl.

Optionally, $R^7$ is substituted with one or more substituted or unsubstituted aryl groups, optionally one or more groups $-(Ar^6)_w$, wherein each $Ar^6$ independently represents a substituted or unsubstituted aryl or heteroaryl group, and w is at least 1, for example 1, 2 or 3.

Optionally, one $R^8$ group is H

Optionally, both $R^8$ groups are not H.

Optionally, at least one $R^8$ is selected from the group consisting of optionally substituted alkyl and $-(Ar^7)_z$, wherein each $Ar^7$ independently represents an optionally substituted aryl or heteroaryl group and z is at least one, optionally 1, 2 or 3.

Optionally, each t is 0.

Optionally, $R^9$ is H.

Optionally, $R^{11}$ is H

Optionally, the polymer further comprises a repeat unit of formula (V):

wherein $Ar^1$ and $Ar^2$ in each occurrence are independently selected from optionally substituted aryl or heteroaryl groups, n is greater than or equal to 1, preferably 1 or 2, R is H or a substituent, preferably a substituent, x and y are each independently 1, 2 or 3, and any two of groups $Ar^1$, $Ar^2$ and R may be linked by a direct bond or a divalent linking group to form a ring.

In a second aspect the invention provides a compound of Formula (Ib):

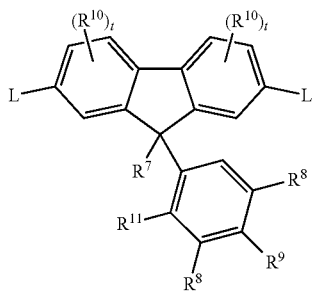

wherein $R^7$ represents a substituent bound to the 9-carbon atom of the fluorene ring through a non-aromatic carbon atom, $R^8$, $R^9$ and $R^{11}$ independently in each occurrence represent H or a substituent with the proviso that at least one $R^8$ is not H; $R^{10}$ independently in each occurrence is a substituent; t in each occurrence is independently 0, 1, 2 or 3; and each L is independently a polymerisable group.

Optionally according to the second aspect, each L is the same or different and is selected from leaving groups capable of participating in metal-mediated cross-coupling.

Optionally according to the second aspect, each L is the same or different and is selected from halogen, boronic acid and esters thereof.

In a third aspect the invention provides a method of forming a polymer comprising the step of polymerizing the compound of the second aspect.

Optionally according to the third aspect, the compound of the second aspect is polymerized in the presence of a metal catalyst.

In a fourth aspect the invention provides a polymer comprising a repeat unit of formula (IIa):

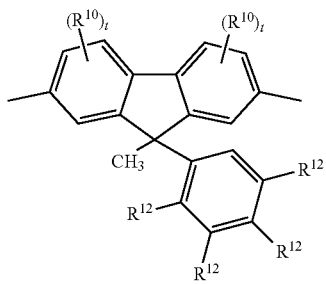

wherein $R^{12}$ independently in each occurrence represent H or a substituent; $R^{10}$ independently in each occurrence is a substituent; and t in each occurrence is independently 0, 1, 2 or 3.

Optionally according to the fourth aspect, at least one $R^{12}$ is H.

Optionally according to the fourth aspect, at least one $R^{12}$ is selected from the group consisting of substituted or unsubstituted alkyl and $-(Ar^7)_z$, wherein each $Ar^7$ independently represents a substituted or unsubstituted aryl or heteroaryl group and z is at least one, optionally 1, 2 or 3.

Optionally according to the fourth aspect, each t is 0.

Optionally according to the fourth aspect, the polymer comprises a repeat unit of formula (V):

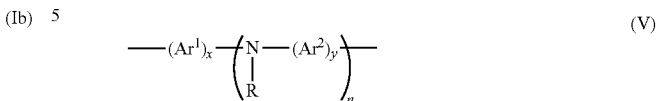

wherein $Ar^1$ and $Ar^2$ in each occurrence are independently selected from substituted or unsubstituted aryl or heteroaryl groups, n is greater than or equal to 1, preferably 1 or 2, R is H or a substituent, preferably a substituent, x and y are each independently 1, 2 or 3, and any two of groups $Ar^1$, $Ar^2$ and R may be linked by a direct bond or a divalent linking group to form a ring.

In a fifth aspect the invention provides a compound of formula (IIb):

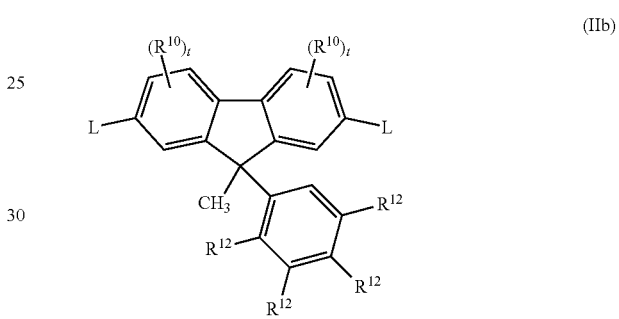

wherein $R^{12}$ independently in each occurrence represents H or a substituent; $R^{10}$ independently in each occurrence is a substituent; t in each occurrence is independently 0, 1, 2 or 3; and each L is independently a polymerisable group.

Optionally according to the fifth aspect, each L is the same or different and is selected from leaving groups capable of participating in metal-mediated cross-coupling.

Optionally according to the fifth aspect, each L is the same or different and is selected from halogen, boronic acid and esters thereof.

In a sixth aspect the invention provides a method of forming a polymer comprising the step of polymerizing the compound of the fifth aspect.

Optionally according to the sixth aspect, the compound of the fifth aspect is polymerized in the presence of a metal catalyst.

In a seventh aspect the invention provides an organic electronic device comprising a polymer according to the first or fourth aspects.

Optionally according to the seventh aspect, the organic electronic device is an organic light-emitting device comprising at least one organic light-emitting layer.

Optionally according to the seventh aspect, the at least one organic light-emitting layer comprises the polymer.

In an eighth aspect, the invention provides use of a repeat unit of formula (III) to increase the stability of a polymer relative to a polymer in which $R^7$ is present in place of Ar or in which Ar is present in place of $R^7$:

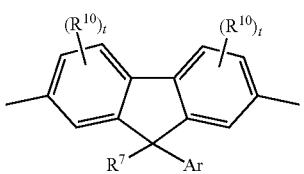

(III)

wherein R⁷ represents a substituent bound to the polymer through a non-aromatic carbon atom; Ar represents an optionally substituted aryl or heteroaryl group; R¹⁰ independently in each occurrence is a substituent; and t in each occurrence is independently 0, 1, 2 or 3.

Optionally according to the eighth aspect, the 9-alkyl substituent is selected from branched and straight chain C1-20 alkyl.

Optionally according to the eighth aspect, Ar is substituted with one or more substituents Optionally according to the eighth aspect, Ar is optionally substituted phenyl group.

Optionally according to the eighth aspect, at least one meta-position of the phenyl group is substituted.

DESCRIPTION OF THE DRAWINGS

The invention will now be described in more detail with reference to the drawings, in which.

DETAILED DESCRIPTION OF THE INVENTION

Figure 1:
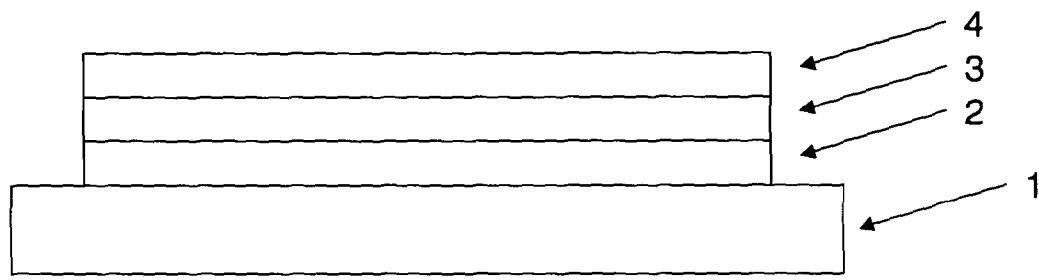
FIG. 1 illustrates an organic light-emitting device according to an embodiment of the invention.

The present inventors have surprisingly found that selection of substituents at the 9-position of a fluorene unit of a polymer may increase stability of the polymer. For example, a polymer comprising 9-aryl-9-alkyl-fluorene repeat units may have longer lifetime that a polymer comprising 9,9-dialkyl and/or 9,9-diaryl fluorene repeat units.

Without wishing to be bound by any theory, it is believed that singlet and/or triplet excited states formed during operation of an organic light-emitting device may directly or indirectly cause scission of bonds of one or more organic materials of the device, thereby limiting the lifetime of the organic light-emitting device. Accordingly, the device lifetime may depend at least in part on stability of the organic materials of the device, in particular the bonds strengths of those materials.

With reference to fluorene repeat units, and again without wishing to be bound by any theory, it is believed that the bond strengths of at least some carbon-carbon bonds within the fluorene repeat unit may depend in part on the identity of substituents at the 9-position of the fluorene repeat unit.

In the case of fluorenes without aryl or heteroaryl substituents in the 9-position such as dialkylfluorene, the weakest bonds are believed to be the bonds between the fluorene C9 atom and the alkyl substituents. In the case of 9,9-di(hetero)arylfluorene, the weakest bonds are believed to be those bonds between the fluorene C9 atom and the adjacent phenyl rings.

Consequently, the weakest bond of a fluorene repeat unit of formula (Ia), (IIa) or (III) may be stronger than the weakest bond of a material such as a 9,9-dialkyl fluorene repeat unit or a corresponding 9,9-di(hetero)aryl fluorene repeat unit, thereby improving overall polymer stability.

R⁷ of formula (Ia), (Ib) or (III) may be optionally substituted alkyl, for example optionally substituted branched or straight chain $C_{1-20}$ alkyl or optionally substituted branched or straight chain $C_{2-20}$ alkyl. This alkyl group may be substituted with one or more groups —(Ar⁶)$_w$, wherein each Ar⁶ independently represents an optionally substituted aryl or heteroaryl group, and w is at least 1, for example 1, 2 or 3. If w is greater than 1 then the Ar⁶ groups may form a linear or branched chain of (hetero)aryl groups. A group —(Ar⁶)$_w$ may be attached to an end of the alkyl group. Exemplary Ar⁶ groups include phenyl and fluorene. Each Ar⁶ group may be substituted with one or more substituents for example one or more alkyl groups, in particular one or more $C_{1-20}$ alkyl groups.

The 9-aryl or 9-heteroaryl group of the repeat unit of formula (IIa) or (III) may be substituted or unsubstituted. In the case where it is substituted it optionally comprises a repeat unit of formula (Ia) illustrated above. The present inventors have found that the bond strength of a C9-phenyl bond is higher if substituents, e.g. alkyl or aryl, are provided at the meta-position rather than the para-position of a 9-phenyl substituent. Exemplary alkyl substituents include $C_{1-20}$ alkyl. Exemplary aryl or heteroaryl substituents include —(Ar⁷)$_z$, wherein each Ar⁷ independently represents an optionally substituted aryl or heteroaryl group, for example phenyl, and z is at least one, optionally 1, 2 or 3. If z is greater than 1 then the Ar⁷ groups may form a linear or branched chain of (hetero)aryl groups. Each Ar⁷ group may be substituted with one or more substituents for example one or more alkyl groups, in particular one or more $C_{1-20}$ alkyl groups. Without wishing to be bound by any theory, it is believed that a substituent in the para-position of a phenyl substituent may serve to stabilize a radical or an ion formed by scission of the C9-phenyl bond whereas meta-substitutions may be less able to mesomerically stabilize radicals or ions and so may encourage bond-breakage less than para-substitutions.

Exemplary 9-alkyl-9-aryl fluorene repeat units include the following.

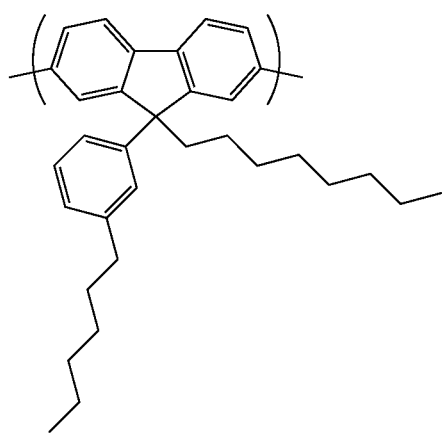

-continued
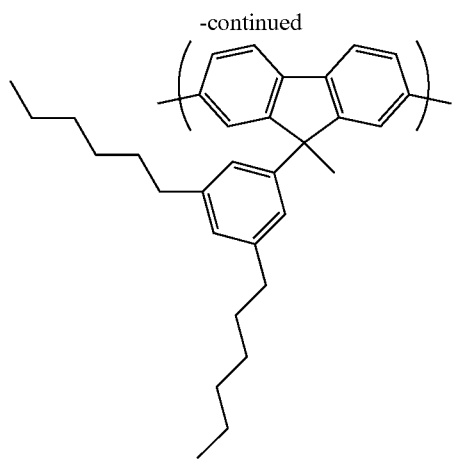
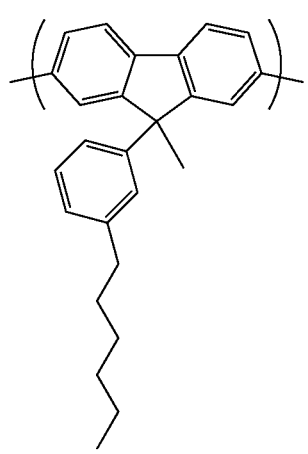
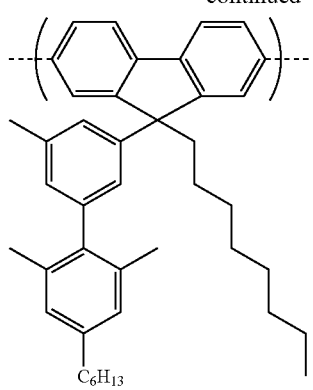
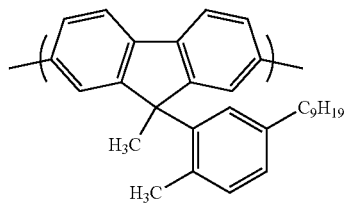
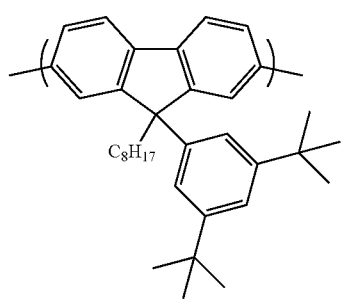
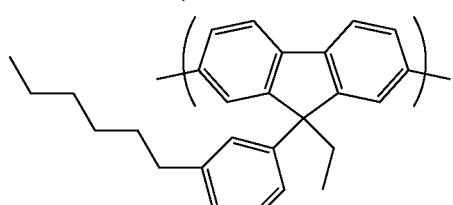
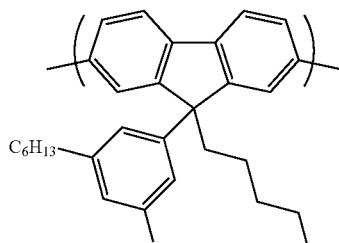

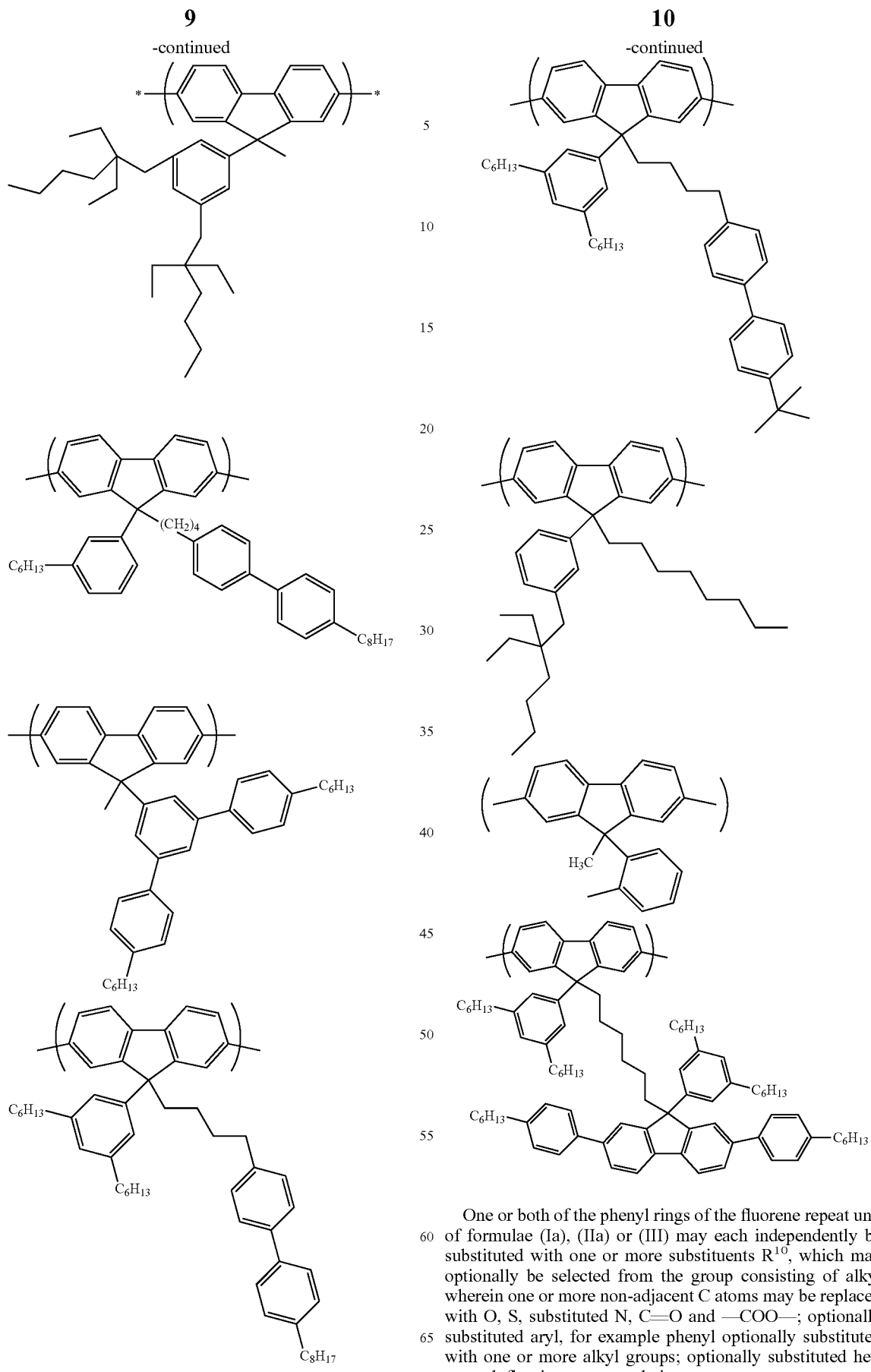

One or both of the phenyl rings of the fluorene repeat unit of formulae (Ia), (IIa) or (III) may each independently be substituted with one or more substituents $R^{10}$, which may optionally be selected from the group consisting of alkyl wherein one or more non-adjacent C atoms may be replaced with O, S, substituted N, C=O and —COO—; optionally substituted aryl, for example phenyl optionally substituted with one or more alkyl groups; optionally substituted heteroaryl; fluorine, cyano and nitro.

In one embodiment, the polymer is a homopolymer comprising repeat units of formula (Ia), (IIa) or (III).

In another embodiment, the polymer is a copolymer comprising one or more repeat units of formula (Ia), (IIa) or (III) and optionally one or more further co-repeat units. In this case, the repeat units of formula (Ia), (IIa) or (III) may be provided in any amount, for example in the range of about 1 mol % to about 99 mol %. Optionally, the repeat unit of formula (Ia), (IIa) or (III) is present in an amount of at least 5 mol %, at least 10 mol % or at least 20 mol %. The copolymer may comprise one or more of hole transporting, electron transporting and/or light-emitting repeat units such as disclosed in, for example, WO 00/55927 and U.S. Pat. No. 6,353,083.

Electron transporting, hole transporting and/or light-emitting units may be provided as repeat units in the polymer backbone, such as disclosed in U.S. Pat. No. 6,353,083, or may be provided as functional units pendent from the polymer backbone.

The polymer is preferably at least partially conjugated along its backbone. Preferably, the fluorene unit is conjugated to at least one, and optionally both, of the repeat units on either side of it in the polymer backbone.

The unit of formula (Ia), (IIa) or (III) may be used as, for example: a repeat unit of a light-emitting polymer, in which this repeat unit and/or another repeat unit is emissive; a repeat unit of a hole transporting polymer comprising one or more hole-transporting repeat units; a repeat unit of an electron-transporting polymer; or as a repeat unit of a host polymer for use in combination with a light-emitting dopant. An emissive polymer may emit, without limitation, red, green or blue light.

Hole Transporting and/or Light-Emitting Repeat Units

One class of hole transporting and/or light-emitting repeat units, for example blue and/or green light-emitting repeat units, are optionally substituted (hetero)arylamines. Suitable repeat units include repeat units of formula (V):

wherein $Ar^1$ and $Ar^2$ in each occurrence are independently selected from optionally substituted aryl or heteroaryl groups, n is greater than or equal to 1, preferably 1 or 2, R in each occurrence is H or a substituent, preferably a substituent, and x and y are each independently 1, 2 or 3.

Exemplary groups R include alkyl, $Ar^3$, or a branched or linear chain of $Ar^3$ groups, for example $—(Ar^3)_v$, wherein $Ar^3$ in each occurrence is independently selected from aryl or heteroaryl and v is at least 1, optionally 1, 2 or 3.

Any of $Ar^1$, $Ar^2$ and $Ar^3$ may independently be substituted with one or more substituents. Preferred substituents are selected from the group $R^3$ consisting of:

alkyl wherein one or more non-adjacent C atoms may be replaced with O, S, substituted N, C=O and —COO— and one or more H atoms of the alkyl group may be replaced with F or aryl or heteroaryl optionally substituted with one or more groups $R^4$, aryl or heteroaryl optionally substituted with one or more groups $R^4$, $NR^5_2$, $OR^5$, $SR^5$, fluorine, nitro and cyano;

wherein each $R^4$ is independently alkyl in which one or more non-adjacent C atoms may be replaced with O, S, substituted N, C=O and —COO— and one or more H atoms of the alkyl group may be replaced with F, and each $R^5$ is independently selected from the group consisting of alkyl and aryl or heteroaryl optionally substituted with one or more alkyl groups.

R may comprise a crosslinkable-group, for example a group comprising a polymerisable double bond such and a vinyl or acrylate group, or a benzocyclobutane group.

Any of the aryl or heteroaryl groups in the repeat unit of Formula (V) may be linked by a direct bond or a divalent linking atom or group. Preferred divalent linking atoms and groups include O, S; substituted N; and substituted C.

Where present, substituted N or substituted C of $R^3$, $R^4$ or of the divalent linking group may independently in each occurrence be $NR^6$ or $CR^6_2$ respectively wherein $R^6$ is alkyl or optionally substituted aryl or heteroaryl. Optional substituents for aryl or heteroaryl groups $R^6$ may be selected from $R^4$ or $R^5$.

In one preferred arrangement, R is $Ar^3$ and each of $Ar^1$, $Ar^2$ and $Ar^3$ are independently and optionally substituted with one or more $C_{1-20}$ alkyl groups.

Particularly preferred units satisfying Formula 1 include units of Formulae 1-3:

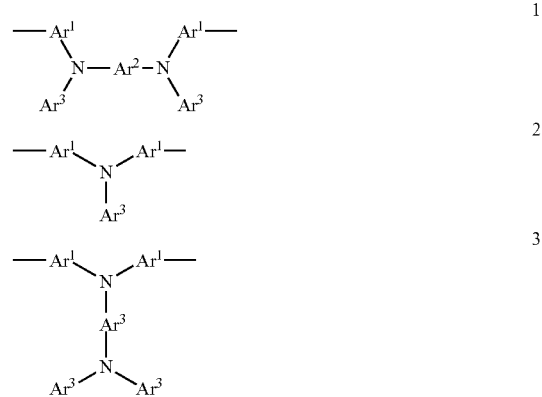

wherein $Ar^1$ and $Ar^2$ are as defined above; and $Ar^3$ is optionally substituted aryl or heteroaryl. Where present, preferred substituents for $Ar^3$ include substituents as described for $Ar^1$ and $Ar^2$, in particular alkyl and alkoxy groups.

$Ar^1$, $Ar^2$ and $Ar^3$ are preferably phenyl, each of which may independently be substituted with one or more substituents as described above.

In another preferred arrangement, aryl or heteroaryl groups of formula (V) are phenyl, each phenyl group being optionally substituted with one or more alkyl groups.

In another preferred arrangement, $Ar^1$, $Ar^2$ and $Ar^3$ are phenyl, each of which may be substituted with one or more $C_{1-20}$ alkyl groups, and v=1.

In another preferred arrangement, $Ar^1$ and $Ar^2$ are phenyl, each of which may be substituted with one or more $C_{1-20}$ alkyl groups, and R is 3,5-diphenylbenzene wherein each phenyl may be substituted with one or more alkyl groups.

The polymer may comprise one, two or more different repeat units of formula (V). For example, the polymer may comprise one repeat unit of formula (V) to provide hole transport and another repeat unit of formula (V) to provide light-emission.

The repeat units of formula (V) may be provided in any amount, for example in the range of about 1 mol % to about 70 mol %. In the case where the polymer is used as a light-emitting material, the repeat units of formula (V) may be present in an amount less than 50 mol %, for example less than 20 mol % or less than 10 mol %.

Arylene Repeat Units

Electron transport may be provided by a conjugated chain of arylene repeat units, for example a conjugated chain comprising one or more of fluorene, indenofluorene, and phenylene repeat units (including repeat units of formula I and II), each of which may optionally be substituted by, for example, alkyl or alkoxy.

Exemplary fluorene repeat units, other than repeat units of formula (I) or (II), include repeat units of formula (IV):

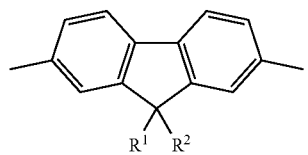

(IV)

wherein $R^1$ and $R^2$ are independently H or a substituent and wherein $R^1$ and $R^2$ may be linked to form a ring. In the case where $R^1$ and $R^2$ are different, they do not form a repeat unit of formula (Ia), (IIa) or (III). In one optional arrangement, $R^1$ and $R^2$ are the same.

$R^1$ and $R^2$ are optionally selected from the group consisting of hydrogen; optionally substituted $Ar^3$ or a linear or branched chain of $Ar^3$ groups, wherein $Ar^3$ is as described above; and optionally substituted alkyl wherein one or more non-adjacent C atoms of the alkyl group may be replaced with O, S, substituted N, C=O and —COO—.

In the case where $R^1$ or $R^2$ comprises alkyl, optional substituents of the alkyl group include F, CN, nitro, and aryl or heteroaryl optionally substituted with one or more groups $R^4$ wherein $R^4$ is as described above.

In the case where $R^1$ or $R^2$ comprises aryl or heteroaryl, each aryl or heteroaryl group may independently be substituted. Preferred optional substituents for the aryl or heteroaryl groups include one or more substituents $R^3$.

Optional substituents for the fluorene unit, other than substituents $R^1$ and $R^2$, are preferably selected from the group consisting of alkyl wherein one or more non-adjacent C atoms may be replaced with O, S, substituted N, C=O and —COO—; optionally substituted aryl, for example phenyl optionally substituted with one or more alkyl groups; optionally substituted heteroaryl; fluorine, cyano and nitro.

Where present, substituted N in repeat units of formula (IV) may independently in each occurrence be $NR^5$ or $NR^6$.

In one preferred arrangement, at least one of $R^1$ and $R^2$ comprises an optionally substituted $C_1$-$C_{20}$ alkyl or an optionally substituted aryl group, in particular phenyl substituted with one or more $C_{1-20}$ alkyl groups.

In the case where fluorene repeat units other than repeat units of formula (Ia), (IIa) or (III) are present, they may optionally be present in a mol percent amount that is less than the mol percent amount of repeat units of formula (Ia), (IIa) or (III).

Polymerisation Methods

Preferred methods for preparation of conjugated polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π—Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, preferably bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

Light-Emitting Dopants

A polymer comprising a repeat unit of formula (Ia), (IIa) or (III) may be used as light-emitting polymer in which the fluorene unit or a co-repeat unit may be luminescent. Alternatively, the polymer may be used as a host material, or as a component of a host material, for one or more fluorescent or phosphorescent light-emitting dopants. Suitable dopants include luminescent metal complexes, for example metal complexes comprising optionally substituted complexes of formula (VI):

$$ML^1_q L^2_r L^3_s \qquad (VI)$$

wherein M is a metal; each of $L^1$, $L^2$ and $L^3$ is a coordinating group; q is an integer; r and s are each independently 0 or an integer; and the sum of (a. q)+(b. r)+(c. s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include:

lanthanide metals such as cerium, samarium, europium, terbium, dysprosium, thulium, erbium and neodymium; and d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals are particularly suitable for emission from triplet excited states. These metals form organometallic complexes with carbon or nitrogen donors such as porphyrin or bidentate ligands of formula (V):

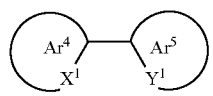

(V)

wherein $Ar^4$ and $Ar^y$ may be the same or different and are independently selected from optionally substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

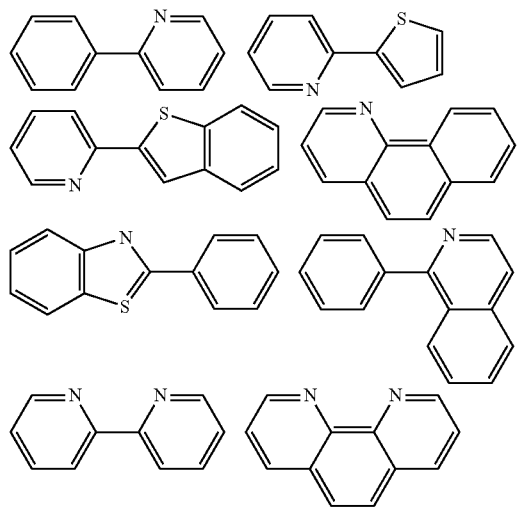

Each of $Ar^4$ and $Ar^y$ may carry one or more substituents. Two or more of these substituents may be linked to form a ring, for example an aromatic ring. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalise the ligand for attachment of further groups as disclosed in WO 02/68435 and EP 1245659; and dendrons which may be used to obtain or enhance solution processability of the metal complex as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the core and dendritic branches comprises an aryl or heteroaryl group.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission colour is determined by the choice of ligand as well as the metal.

A wide range of fluorescent low molecular weight metal complexes are known and have been demonstrated in organic light emitting devices [see, e.g., Macromol. Sym. 125 (1997) 1-48, U.S. Pat. No. 5,150,006, U.S. Pat. No. 6,083,634 and U.S. Pat. No. 5,432,014]. Suitable ligands for di or trivalent metals include: oxinoids, e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), schiff bases, azoindoles, chromone derivatives, 3-hydroxyflavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission colour.

The host and the light-emitting dopant may be physically mixed. Alternatively, the light-emitting dopant may be chemically bound to the host. In the case of a polymeric host, the light-emitting dopant may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

This binding may result in more efficient transfer of excitons from the host polymer to the light emitting dopant because it may provide intramolecular exciton transfer pathways unavailable to a corresponding mixed system.

Moreover, binding may be beneficial for processing reasons. For example, if the light emitting dopant has low solubility then binding it to a soluble polymer allows the light emitting dopant to be carried in solution by the charge transporting material, enabling device fabrication using solution processing techniques. Furthermore, binding the light emitting dopant to the polymer may prevent phase separation effects in solution-processed devices that may be detrimental to device performance.

More than one light-emitting dopant may be used. For example, red, green and blue light-emitting dopants may be used to obtain white light emission. The 9-alkyl-9-aryl fluorene unit may also emit light, in particular blue light, that may be combined with emission from one or more further dopants to achieve white light emission.

Hole Injection Layers

A conductive hole injection layer, which may be formed from a conductive organic or inorganic material, may be provided between the anode 2 and the light-emitting layer 3 illustrated in FIG. 1 to assist hole injection from the anode into the layer or layers of semiconducting polymer. Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nation®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Charge Transporting Layers

A hole transporting layer may be provided between the anode 2 and the light-emitting layer 3. Likewise, an electron transporting layer may be provided between the cathode and the light-emitting layer.

Similarly, an electron blocking layer may be provided between the anode 2 and the light-emitting layer 3 and a hole blocking layer may be provided between the cathode 4 and the light-emitting layer 3. Transporting and blocking layers may be used in combination. Depending on its HOMO and LUMO levels, a single layer may both transport one of holes and electrons and block the other of holes and electrons.

If present, a hole transporting layer located between anode 2 and light-emitting layer 3 preferably has a HOMO level of less than or equal to 5.5 eV, more preferably around 4.8-5.5 eV. HOMO levels may be measured by cyclic voltammetry, for example.

If present, an electron transporting layer located between light-emitting layer 3 and cathode 4 preferably has a LUMO level of around 3-3.5 eV. For example, a layer of a silicon monoxide or silicon dioxide or other thin dielectric layer having thickness in the range of 0.2-2 nm is provided between light-emitting layer 3 and layer 4.

A hole transporting layer may contain a polymer comprising hole transporting repeat units of formula (I); likewise, an electron transporting layer may contain a polymer comprising electron transporting repeat units of formula (I).

Cathode

Cathode 4 is selected from materials that have a workfunction allowing injection of electrons into the light-emitting layer. Other factors influence the selection of the cathode such as the possibility of adverse interactions between the cathode and the light-emitting material. The cathode may consist of a single material such as a layer of aluminium. Alternatively, it may comprise a plurality of metals, for example a bilayer of a low workfunction material and a high workfunction material such as calcium and aluminium as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

Suitable solvents for forming compositions of the polymer for solution processing include many common organic solvents, such as mono- or poly-alkylbenzenes such as toluene and xylene.

Particularly preferred solution deposition techniques including printing and coating techniques such spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, roll printing and screen printing.

EXAMPLES

Monomer Example 1

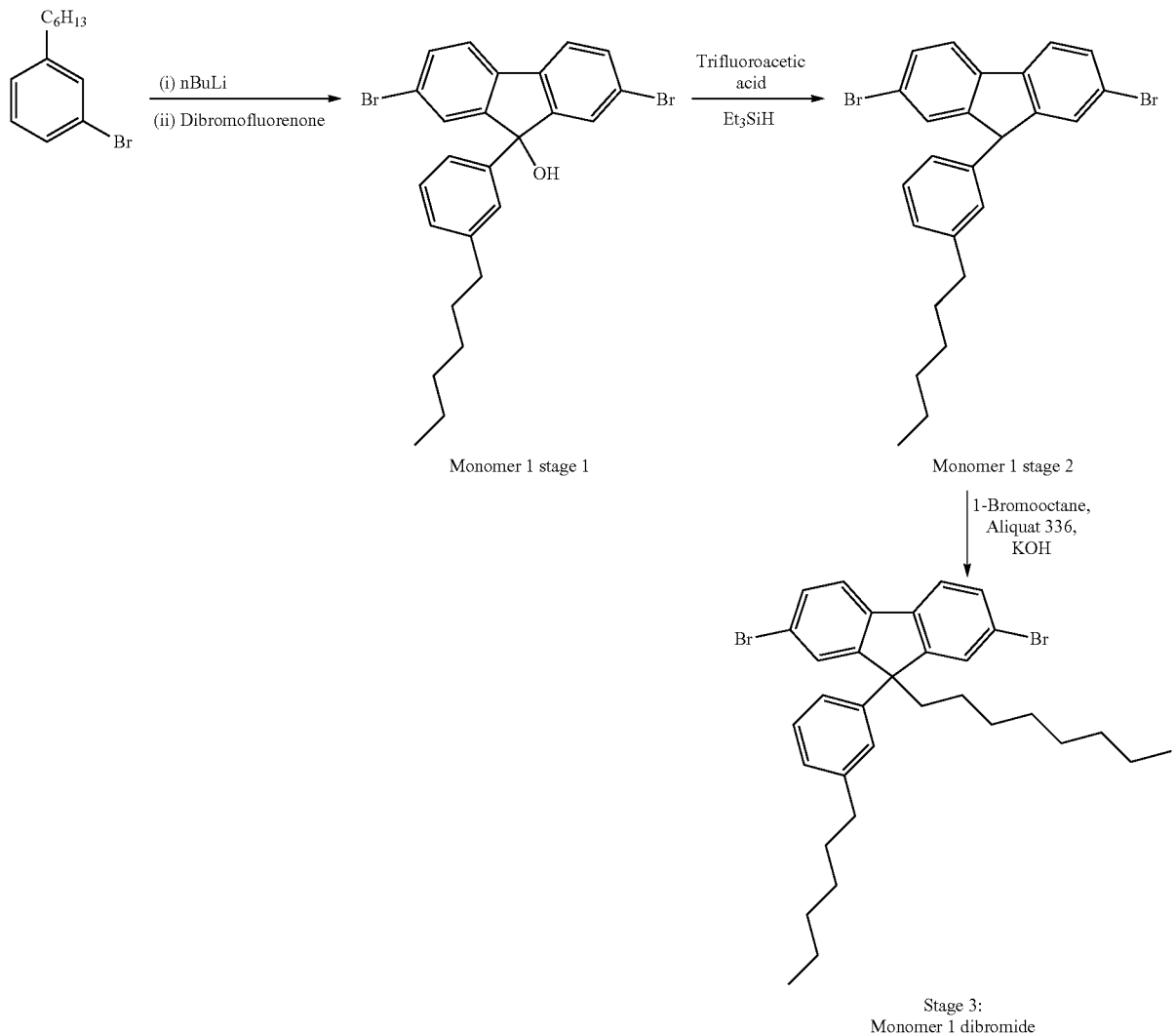

Monomer 1 stage 1

Monomer 1 stage 2

Stage 3:
Monomer 1 dibromide

Monomer 1 Experimental Procedure

Monomer 1 Stage 1

Bromo-3-n-hexylbenzene (111.1 g, 0.46 mol) were dissolved in anhydrous THF (2 L) under nitrogen. The mixture was cooled to <−75° C. n-Butyllithium (2.5 M in hexanes, 176 mL, 0.44 mol) was added drop-wise to the stirred reaction mixture at such a rate as to keep the temperature below −70° C. Dibromofluorenone (142 g, 0.42 mol) was added in portions to the reaction mixture ensuring the internal temperature did not rise above-70° C. The mixture was allowed to warm to RT overnight with stirring, was then cooled to <0° C. and then quenched by the addition of dilute hydrochloric acid (2M, 100 ml). The mixture was allowed to warm to RT. The crude mixture was transferred to a round-bottomed flask and the solvent removed under vacuum. Hexane (2.5 L) was added and the unreacted dibromofluorenone solid was removed by filtration using a fluted filter paper. The hexane filtrate was then washed with water (2×150 ml) and brine (200 ml). The hexane solution was passed through a silica plug, which was eluted with hexane then hexane:DCM (1:1, 3.5 L) and the filtrates were combined and evaporated to yield a dark orange oil (162 g) containing Monomer 1 stage 1 in a 77% yield. (97% purity, GCMS)

Monomer 1 Stage 2

To a mixture of Monomer 1 stage 1 (162 g, 0.33 mol) and trifluoroacetic acid (245 ml, 3.3 mol) was added triethylsilane (115 ml, 0.72 mol). The mixture was then stirred at room temperature for 62 h under nitrogen. The reaction mixture was quenched into water (1 L) and extracted with hexane. The combined hexane phases were washed with a potassium phosphate solution (500 ml, 10% wt/vol). The aqueous phase was removed and the hexane phase was washed with brine (300 ml). The organic phase was evaporated under vacuum to give an orange coloured oil. The oil was dissolved in dichloromethane (~400 ml) and precipitated into methanol (2.5 L). The light yellow solid was filtered off, rinsed with methanol, and dried under vacuum at 60° C. to yield Monomer 1 stage 2. (138 g, 88% yield, 97.8% GCMS purity) This was used directly in the next stage.

Monomer 1 Dibromide

A mixture of Monomer 1 stage 2 (138 g, 0.28 mol), 1-bromooctane (75.4 ml, 0.43 mol) and Aliquat® (1.16 g, 0.003 mol) was heated to 85° C. (oil bath temperature) with stirring. Potassium hydroxide solution (40% aq., 60 ml, 0.72 mol) was added dropwise to the reaction mixture. The mixture was stirred at this temperature for 24 hours. After the reaction was completed, water (200 ml) was added to the reaction mixture, followed by dichloromethane (400 ml). The aqueous phase was separated, washed with dichloromethane (200 ml), and the organic phases were combined and washed with water (2×300 ml). The dichloromethane phase was added dropwise to a beaker containing methanol (2 L) followed by IL of methanol. The cream coloured solid formed was filtered and washed with methanol. It was recrystallised from toluene/acetonitrile to give Monomer 1 dibromide in 99.48% HPLC purity (145 g, 85% yield). Further recrystallisation from acetonitrile/toluene on 65 g of this material provided Monomer 1 dibromide as a fine white powder (99.74% HPLC, 40.5 g, 65% yield).

Monomer Example 2

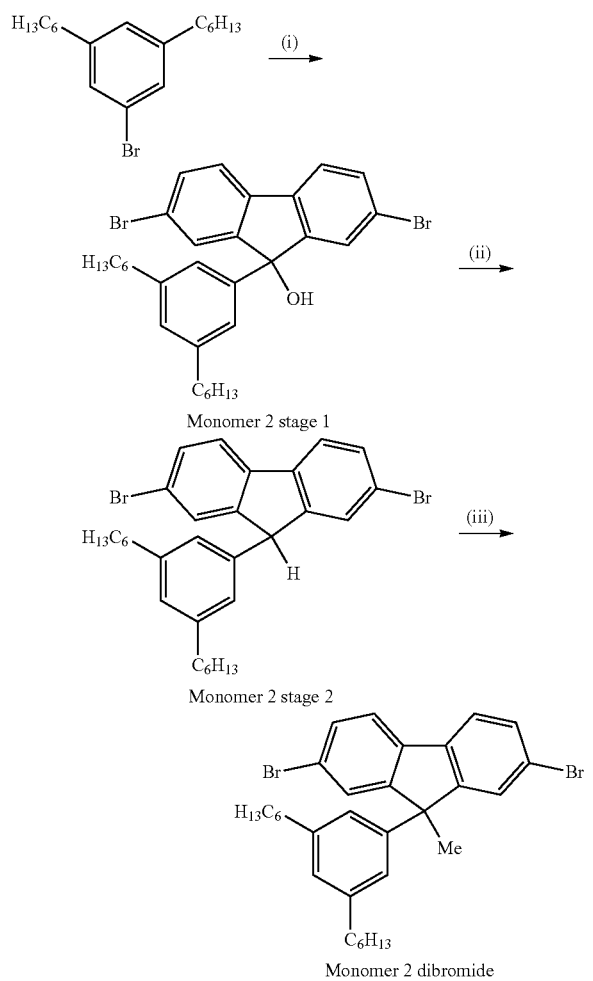

Monomer 2 dibromide (i) a) n-BuLi, THF, -76° C., b) 2,7-Dibromofluorenone, -76° C. to r.t;
(ii) Et$_3$SiH, TFA, Hexane, r.t.;
(iii) MeI, KOH, DMSO/H$_2$O, r.t.

Monomer 2 Experimental Procedure

Monomer 2 Stage 1

Monomer 2 stage 1 was prepared after a similar procedure described for Monomer 1 stage 1 starting from 1-Bromo-3,5-di-n-hexylbenzene (292.0 g, 0.8976 mol) and 2,7-dibromofluorenone (275.8 g, 0.8160 mol). This yielded crude monomer 2 stage 1 (428.2 g).

Monomer 2 Stage 2

Conversion of 428.2 g of Monomer 2 stage 1 after a similar procedure described for Monomer 1 stage 2 yielded Monomer 2 stage 2 (489.9 g, 87% yield, 98.5% GCMS purity).

Monomer 2 stage 3

A mixture of Monomer 2 stage 2 (368.7 g, 0.6486 mol), dimethyl sulfoxide (1.6 L), water (45 ml) and potassium hydroxide (145.58 g, 2.5945 mol) were placed into a flask. Nitrogen was bubbled through the resulting dark red mixture using a pipette for 1 hour while stirring. Methyl iodide (121.1 ml, 1.9459 mol) was added drop wise at such a rate as to keep the internal temperature below 25° C. The resulting pale orange mixture was stirred at room temperature over night. After the reaction was complete, water (500 ml) was added to the mixture followed by hexane (500 ml). The dark brown mixture was stirred for 1 hr, transferred to a separating funnel and the two phases were separated. The aqueous phase was extracted with hexane (2×400 ml), the organic phases were combined, washed with water (3×400 ml, pH7) and brine (400 ml). The solvent was removed under reduced pressure to yield an orange oil. The oil was dissolved in hexane (500 ml), filtered through a silica plug (Ø 9 cm×6 cm, packed with hexane), eluted with hexane (1.5 L) followed by hexane/dichloromethane (80:20, 1.0 L). Fractions containing M035 dibromide were combined and solvent was removed under vacuum to give a yellow oil. The oil was dissolved in dichloromethane (300 ml) precipitated into methanol (4.0 L); the oily mixture was stirred for 3 hrs. The now slurry was filtered and the resulting white solid was washed with methanol. The solid (200 g) was recrystallised from methanol and n-butyl acetate. The resulting white solid was isolated by filtration, washed with methanol (~200 ml) and air dried for several hours. Recrystallisation was repeated until the desired purity of >99.6% by HPLC was achieved. The product was then dried in under vacuum at 40° C. to constant weight. 127 g Monomer 2 dibromide were isolated as a white solid to yield (33.7% yield, 99.64% by HPLC).

Polymer Examples

A blue light-emitting polymer was formed by Suzuki polymerization as described in WO 00/53656 of Monomer Example 1 and the following further monomers:

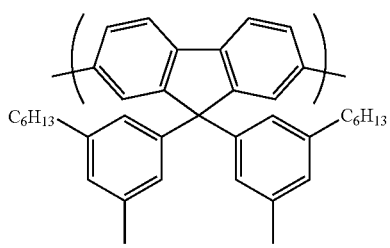
Monomer3
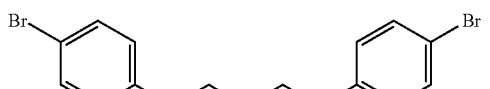
Monomer8 diBr
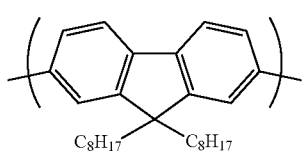
Monomer4
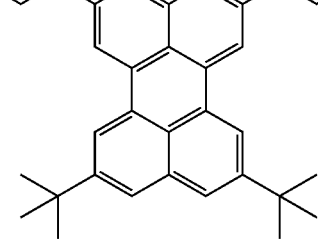
Monomer9 diBr
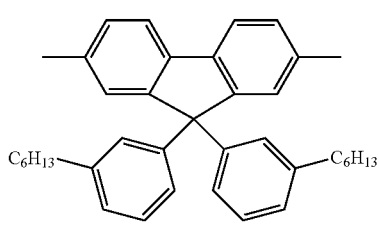
Monomer5
Monomer 7 was prepared according to the method described in WO 2010/001982.
Monomer 9 was prepared according to the following method:
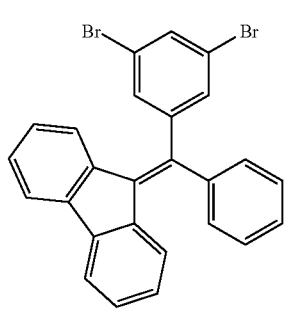
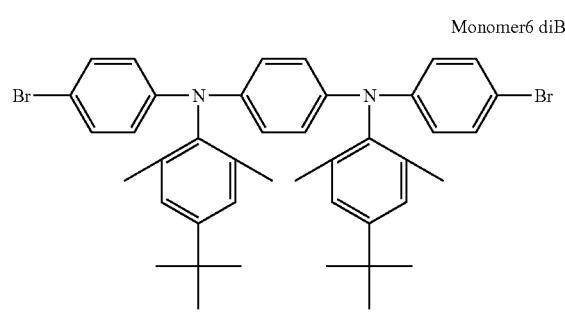
Monomer6 diBr
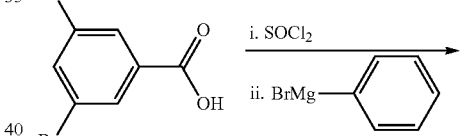
Monomer 9 Intermediate
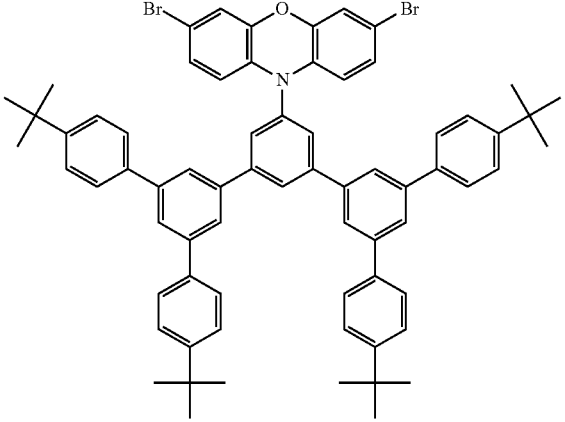
Monomer7 diBr
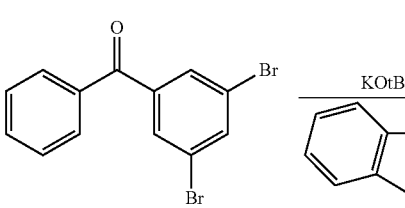
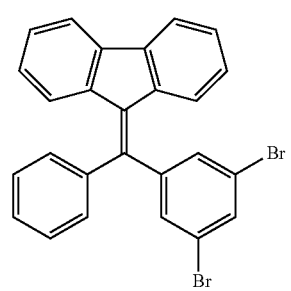
Monomer 9

Thionyl chloride (100 ml) was added to 3,5-dibromobenzoic acid (50.0 g, 178 mmoles) and heated at reflux for 6 hours. The excess thionyl chloride was then removed by distillation and the remaining brown solid was dissolved in dry tetrahydrofuran (1 L) and cooled to below −70° C. under nitrogen in an acetone/dry ice bath. Phenyl magnesium bromide solution (179 ml, 1M in tetrahydrofuran, 179 mmoles) was added dropwise to the cold reaction mixture and the temperature was then allowed to rise to room temperature while stirring for 4 hours. Water (200 ml) was cautiously added followed by diethyl ether (200 ml). The aqueous layer was separated and extracted with diether ether (2×50 ml) and then combined organic layers were washed with water (3×100 ml), dried over magnesium sulphate and evaporated. Trituration with methanol released a white solid which, after recrystallisation from hexane, gave the Monomer 9 intermediate (23.66 g).

Potassium tert-butoxide (39.16 g, 342 mmoles) was added to a solution of fluorene (58.0 g, 342 mmoles) in dry tetrahydrofuran (400 ml) under nitrogen and stirred at room temperature until fully dissolved. The reaction mixture was then cooled down to −75° C. and a solution of 3,5-dibromobenzophenone (116.3 g, 342 mmoles) in dry tetrahydrofuran (350 ml) was added dropwise, maintaining the temperature below −70° C. and then stirred overnight while allowing to warm to room temperature. The reaction was then cooled and aqueous ammonium chloride (sat., 250 ml) was added and stirred at 0° C. for 20 minutes and then the tetrahydrofuran was removed under vacuum. Water (1 L) was added and extracted with dichloromethane (3×250 ml) and the combined organic fractions were washed with water (3×300 ml), dried over magnesium sulfate and evaporated to give a brown oil. Purification by column chromatography (hexane+increasing dichloromethane) followed by trituration with hexane and recrystallisation from dichloromethane:methanol gave Monomer 9 as a pale yellow solid (38.2 g).

Polymers:

Polymers were synthesized as described in WO 00/53656 from 50% dipinacoldiesters and 50% dibromides:

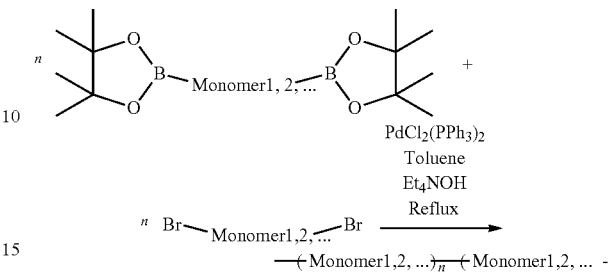

Monomer 1, 2 . . . can be one or more different esters or bromides to result in random copolymers.

Polymer Compositions:

| Polymer | Diester feed [diE] | Dibromide feed [diBr] | Mp | Mn | Pd |
|---|---|---|---|---|---|
| PolymerA (Comparative) | 36% Monomer3 14% Monomer4 | 43.75% Monomer5 5% Monomer6 1% Monomer7 0.25% Monomer8 | 1,217,000 | 336,000 | 4.27 |
| PolymerB | 36% Monomer3 14% Monomer4 | 43.75% Monomer1 5% Monomer6 1% Monomer7 0.25% Monomer8 | 1,078,000 | 318,000 | 4.11 |
| PolymerC (Comparative) | 50% Monomer3 | 30% Monomer5 13.8% Monomer4 5% Monomer6 1% Monomer7 0.2% Monomer9 | 1,088,000 | 408,000 | 3.11 |
| PolymerD | 50% Monomer2 | 30% Monomer1 13.8% Monomer4 5% Monomer6 1% Monomer7 0.2% Monomer9 | 954,000 | 292,000 | 3.91 |

Device Examples

Organic light-emitting devices having the following structure were formed:

ITO/HIL/HTL/LE/Cathode wherein HIL is a hole-injecting layer comprising a hole-injecting material, HTL is a hole-transporting layer formed by spin-coating a light-emitting polymer comprising fluorene repeat units of formula (IV) and amine repeat units of formula (V), LE is a light-emitting layer formed by spin-coating Polymer A, B, C or D; and the cathode comprises a trilayer structure of a metal fluoride, aluminium and silver.

Figure 2:
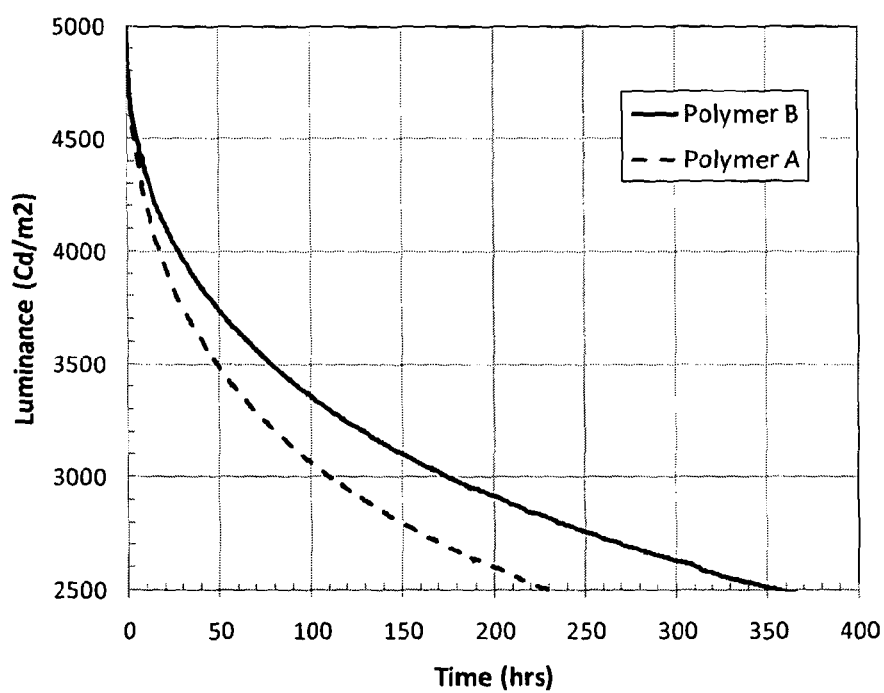
FIG. 2 illustrates lifetimes of an organic light-emitting device according to an embodiment of the invention and a comparative device.

Stability of the polymer was determined by measuring the time taken for brightness of the device to fall to 50% of an initial luminance. As shown in FIG. 2, the comparative device containing polymer A in the light-emitting layer has a substantially shorter lifetime than the device containing polymer B, which contains asymmetrically substituted fluorene monomers.

Figure 3:
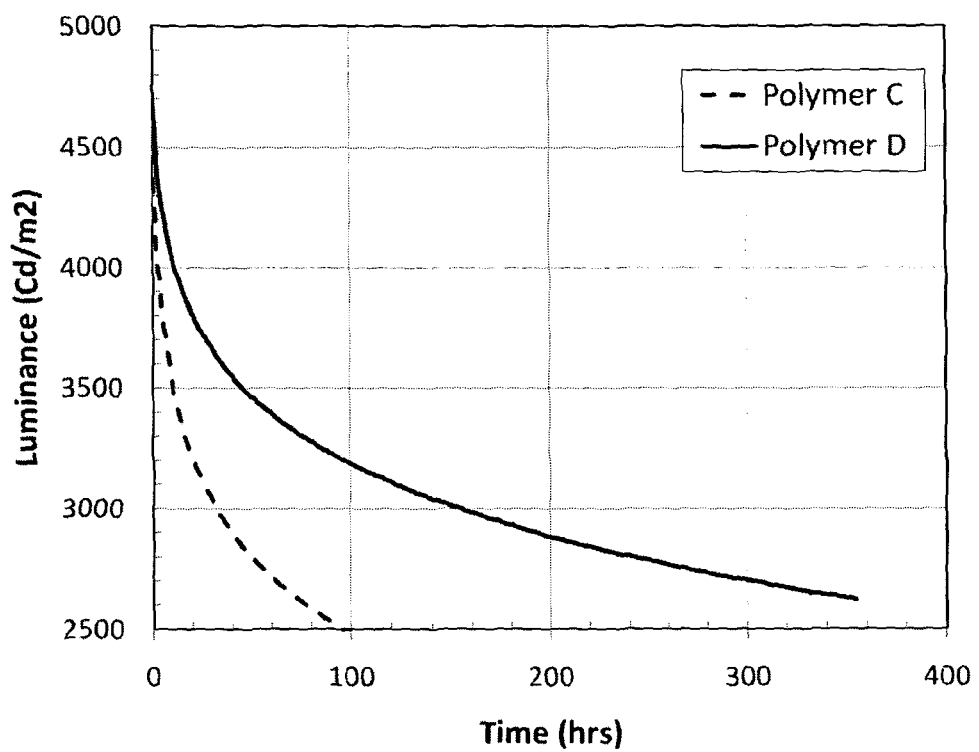
FIG. 3 illustrates lifetimes of an organic light-emitting device according to an embodiment of the invention and a comparative device.

Likewise with reference to FIG. 3, the comparative device containing polymer C in the light-emitting layer has a substantially shorter lifetime than the device containing polymer B, which contains asymmetrically substituted fluorene monomers.

Polymer Stability

The comparative lifetime data of the device examples illustrate the increased stability obtained by incorporation of a repeat unit of formula (Ia), (IIa) or (III).

The table below provides bond lengths obtained by molecular modeling of the following fluorene unit:

|  |  | Bond length (Angstroms) | | | |
|---|---|---|---|---|---|
| Substituent A | Substituent B | a | B | c | d |
| n-octyl | n-octyl | 1.529 | 1.529 | 1.558 | 1.558 |
| n-octyl | 3-(n-hexyl)phenyl | 1.534 | 1.534 | 1.557 | 1.545 |
| n-octyl | 3,5-di(n-hexyl)phenyl | 1.534 | 1.534 | 1.557 | 1.545 |
| Methyl | Methyl | 1.529 | 1.529 | 1.545 | 1.545 |
| Methyl | 3,5-di(n-hexyl)phenyl | 1.534 | 1.534 | 1.547 | 1.539 |

Modelling was performed at density functional level of theory using the B3LYP functional and 6-31 g* basis set as implemented in Gaussian 09, Revision A.02, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Foresman, J. V. Ortiz, J. Cioslowski, and D. J. Fox, Gaussian, Inc., Wallingford Conn., 2009.

It is apparent from the above table that, in these examples, at least one of the weakest bonds of the dioctylfluorene or dimethylfluorene unit (bonds c and d, which have the longest bond length of this unit) is stabilised by replacement of one octyl group with a meta-substituted phenyl group. Additionally, in these examples the difference between the weakest and strongest of bonds a, b, c and d, and/or the variance of these four bond strengths from a mean bond strength of the four bonds, is reduced.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A polymer comprising a repeat unit of formula (Ia):

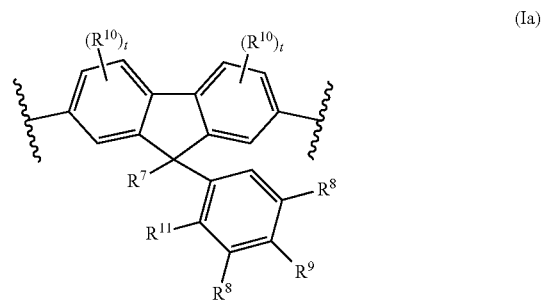

(Ia)

wherein $R^7$ represents a substituent directly bound to the 9-carbon atom of the fluorene ring through a non-aromatic carbon atom of $R^7$; $R^8$, $R^9$ and $R^{11}$ independently in each occurrence represent H or a substituent with the proviso that at least one $R^8$ is not H; $R^{10}$ independently in each occurrence is a substituent; and t in each occurrence is independently 0, 1, 2 or 3.

2. A polymer according to claim 1 wherein $R^7$ is a substituted or unsubstituted alkyl.

3. A polymer according to claim 2 wherein the substituted or unsubstituted alkyl is a substituted or unsubstituted linear alkyl.

4. A polymer according to claim 2 wherein $R^7$ is substituted with one or more substituted or unsubstituted aryl groups.

5. A polymer according to claim 4 wherein the one or more substituted or unsubstituted aryl groups are one or more groups —$(Ar^6)_w$, wherein each $Ar^6$ independently represents a substituted or unsubstituted aryl or heteroaryl group, and w is at least 1.

6. A polymer according to claim 5 wherein w is 1, 2, or 3.

7. A polymer according to claim 1 wherein one $R^8$ group is H.

8. A polymer according to claim 1 wherein both $R^8$ groups are not H.

9. A polymer according to claim 1 wherein at least one $R^8$ is selected from the group consisting of substituted or unsubstituted alkyl and —$(Ar^7)_z$, wherein each $Ar^7$ independently represents a substituted or unsubstituted aryl or heteroaryl group and z is at least 1.

10. A polymer according to claim 9 wherein z is 1, 2, or 3.

11. A polymer according to claim 1 wherein each t is 0.

12. A polymer according to claim 1 wherein $R^9$ is H.

13. A polymer according to claim 1 wherein $R^{11}$ is H.

14. A polymer according to claim 1 comprising a repeat unit of formula (V):

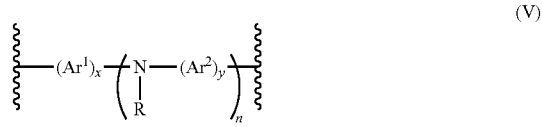

(V)

wherein $Ar^1$ and $Ar^2$ in each occurrence are independently selected from substituted or unsubstituted aryl or heteroaryl groups, n is greater than or equal to 1, R is H or a substituent, x and y are each independently 1, 2 or 3, and any two of groups $Ar^1$, $Ar^2$ and R may be linked by a direct bond or a divalent linking group to form a ring.

15. A polymer according to claim 14 wherein n is 1 or 2.

16. A polymer according to claim 14 wherein R is a substituent.

17. An organic electronic device comprising a polymer according to claim 1.

18. An organic electronic device according to claim 17 that is an organic light-emitting device comprising at least one organic light-emitting layer.

19. An organic electronic device according to claim 18 wherein the at least one organic light-emitting layer comprises the polymer.

* * * * *